(12) United States Patent
Li

(10) Patent No.: US 10,566,089 B1
(45) Date of Patent: Feb. 18, 2020

(54) NANOSENSOR ARRAY FOR MEDICAL DIAGNOSES

(71) Applicant: The USA as Represented by the Administrator of the National Aeronautics & Space Administration (NASA), Washington, DC (US)

(72) Inventor: Jing Li, San Jose, CA (US)

(73) Assignee: United States of America as Represented by the Administrator of NASA, Washington, DC (US)

(*) Notice: Subject to any disclaimer, the term of this patent is extended or adjusted under 35 U.S.C. 154(b) by 991 days.

(21) Appl. No.: 13/725,475

(22) Filed: Dec. 21, 2012

(51) Int. Cl.
G01N 33/48 (2006.01)
G01N 33/50 (2006.01)
G16H 50/20 (2018.01)
A61B 5/087 (2006.01)

(52) U.S. Cl.
CPC ............. G16H 50/20 (2018.01); A61B 5/087 (2013.01)

(58) Field of Classification Search
None
See application file for complete search history.

(56) References Cited

U.S. PATENT DOCUMENTS

| 6,974,706 | B1 | 12/2005 | Melker et al. |
| 7,948,041 | B2 | 5/2011 | Bryant et al. |
| 7,992,422 | B2 | 8/2011 | Leddy et al. |
| 8,080,206 | B2 | 12/2011 | Leddy et al. |
| 2004/0137637 | A1 | 7/2004 | Wang et al. |
| 2005/0151214 | A1* | 7/2005 | Gole ............. G01N 27/127 257/414 |
| 2012/0065534 | A1 | 3/2012 | Rigas |

FOREIGN PATENT DOCUMENTS

WO WO2011068976 A1 6/2011

OTHER PUBLICATIONS

Gautam et al. Detection of organic vapors by graphene films functionalized with metallic nanoparticles. Journal of Applied Physics, vol. 112, Dec. 11, 2012, article 114326, 8 pages.*

(Continued)

Primary Examiner — Russell S Negin
(74) Attorney, Agent, or Firm — Rhys W. Cheung; Robert M. Padilla

(57) ABSTRACT

A method for sensing presence of at least one specified chemical component in a patient's sample gas, associated with a disease (or medical condition), and for associating presence of the disease with presence of the specified chemical component concentration in an identified concentration range. Pattern matching is applied to identify one or more specified components that are present in the sample gas. Measured electrical parameter values (EPVs) for each nanosensor are modeled by constitutive relations dependent on a polynomial of powers of component concentrations. The EPV models are used to estimate component concentrations for the differently functionalized nanosensors. Estimated concentrations are averaged over the sensors to provide an overall concentration value for each surviving specified component. These overall concentration values are compared with concentration ranges associated, to estimate presence or absence of a disease or medical condition.

18 Claims, 6 Drawing Sheets

(56) References Cited

OTHER PUBLICATIONS

Gouma et al. Nanosensor and breath analyzer for ammonia detection in exhaled human breath. IEEE Sensors Journal, vol. 10, 2010, pp. 49-53.*

Abaffy, et al., Differential Volatile Signatures from Skin, Naevi and Melanoma: A Novel Approach to Detect a Pathological Process, Open Access, Nov. 4, 2010, vol. 5-11, PLoS ONE, www.plosone.org.

Aetna, Analysis of Volatile Organic Compounds to Detect Bacteriuria, Clinical Policy Bulletin: Analysis of Volatile Organic Compounds to Detect Bacteria, Oct. 4, 2005, No. 0717, http://www.aetna.com/cpb/medical/data/700_799/0717.html.

Avouac, et al., Angiogenic biomarkers predict the occurrence of digital ulcers in systemic sclerosis, Clinical and Epidemiological Research, Nov. 15, 2011, group.bmj.com.

Buszewski, et al., Human exhaled air analytics: biomarkers of diseases, Biomedical Chromatography, Apr. 12, 2007, 553-566, 21, John Wiley & Sons, Ltd.

Cao, et al., Breath Analysis: Potential for Clinical Diagnosis and Exposure Assessment, Clinical Chemistry, Mar. 2, 2006, 800-811, 52-5.

Crofford, et al., Acetone in Breath and Blood, Transactions of the American Clinical and Climatological Association, 1977, 128-139, Vanderbilt University School of Medicine, Department of Medicine.

Miekisch, et al., Analysis of Volatile Disease Markers in Blood, Clinical Chemistry, Jun. 2001, 1053-1060, 47-6, American Association for Clinical Chemistry.

Peng, et al., Detecting Simulated Patterns of Lung Cancer Biomarkers by Random Network of Single-Walled Carbon Nanotubes Coated with Nonpolymeric Organic Materials, Nano Letters Oct. 8, 2003, 3631-3635, 8-11, American Chemical Society.

Salomaa, et al., Thirty-One Novel Biormarkers as Predictors for Clinically Incident Diabetes, Open Access, Apr. 9, 2010, PLoS ONE, www.piosone.org.

Turner, et al., Electronic noses and diseases diagnostics, Nature Reviews | Microbiology, Feb. 2004, 161-166, 2.

University Relations News Bureau, MSU scientists invent breathalyzer to detect diabetes Mississippi State University, Jun. 8, 2004, http://www.msstate.edu/web/media/detail.php?id=2500.

Wang, et al., An Acetone Nanosensor for Noninvasive Diabetes Detection, Proceedings of AIP Conference 2009, 2009, 206-208, American Institute of Physics.

Wang, et al., Nanosensor Device for Breath Acetone Detection, Sensor Letters, 2010, 1-4, 8-5, American Scientific Publishers, USA.

* cited by examiner

NANOSENSOR ARRAY FOR MEDICAL DIAGNOSES

ORIGIN OF THE INVENTION

The invention described herein was made by employees of the United States Government and may be manufactured and used by or for the Government of the United States of America for governmental purposes without the payment of any royalties thereon or therefor.

FIELD OF THE INVENTION

This invention relates to use of various nanostructures to form a sensor array to detect the presence of an identified set of biomarkers associated with certain diseases or medical conditions for medical diagnosis.

BACKGROUND OF THE INVENTION

An aroma of decaying apples, later identified as acetone, was noted by a physician, John Rollo, in 1796 in a patient with severe diabetes. Various quantitative methods for detecting presence or absence of acetone were subsequently developed for purposes of detecting diabetes in a patient. These methods included gas chromatography with flame ionization detection. Presence of other substances, such as NO, $H_2O_2$, carbonyl sulfide, dimethyl sulfide, pentane, methane, isoprene and/or isopentane have been noted in a patient's breath, in association with other diseases. The detection methods for a particular biomarker are often complex and time consuming, and presence of a given biomarker (referred to herein as a "specified component") is often consistent with presence of any of several diseases. For example, presence of NO in a patient's breath may indicate that the patent has one or more of asthma, COPD, cystic fibrosis and/or lung cancer, among other maladies.

What is needed is a method that is relatively simple, requires no more than about 60 sec to complete, is quantitatively specific for identification of a particular disease or medical condition, and uses a minimum number of chemical or physical tests that can be performed, simultaneously or sequentially, to indicate presence of one disease or medical condition, where possible. Preferably, the system should permit detection of presence of a given biomarker, associated with an identified disease or medical condition, down to a few parts per billion (ppb) concentration.

SUMMARY OF THE INVENTION

The invention meets these needs for certain diseases and medical conditions (referred to collectively herein as a "disease D") by providing a method and associated system that relies upon exposure of a patient's exhaled breath, or similar vapors or gases (collectively referred to as "gases" herein) associated with the patient's body, to a collection or array of sub-arrays of nanostructures ("NSs"), including but not limited to carbon NSs, with each sub-array of one, two or more NSs being functionalized to be sensitive to presence of one or a few biomarkers associated with a given disease D. Pattern recognition techniques are applied to distinguish between a test subject (patient sample gas) with an identifiable disease D and a normal, healthy test subject (healthy sample gas or "HS" gas), preferably collected from one or more healthy other persons that are known to have none of the diseases D. Each different combination of a substrate (e.g., metal, semi-metal, polymer, carbon-based substance, etc.) and functionalization process (e.g., doping, coating, etc.) that is used here is treated as a different sensor.

FIG. 1 graphically illustrates a time dependent function that is measured for $NO_2$ and used to implement the analysis. The function EPV(t;meas), representing an electrical parameter value, is measured and recorded for a selected electrical parameter value, such as electrical current, voltage difference, resistance, impedance, conductance or capacitance associated with an electrical circuit that is partly or wholly constructed using nanostructures ("NSs") that may be, but need not be, carbon-based. A suitable measurement arrangement is illustrated in FIG. 2.

In FIG. 1, the curve EPV(t;meas) has an initial value EPV(t=0;meas), before introduction of a gas or fluid that will perturb the measured value. A difference, $\Delta$EPV(t;q; meas)=EPV(t;q;meas)−EPV(t=0;q;meas), between an initial measured EPV value and a currently measured EPV value will thus be initially 0 and will deviate from 0 with passage of time as a result of exposure of certain surfaces of the NS to the gas or fluid, beginning at time t=t1, shut-off of additional gas or withdrawal of accumulated gas (t2≤t≤t3), and repetition of the cycle (t>t3). The increment quantity $\Delta$EPV(t;q;meas) will at first increase (or decrease) in amplitude, then approach a plateau, then decrease (or increase) in amplitude toward (but not necessarily reach) the initial amplitude EPV(t=0;meas).

For purposes of illustration, it is assumed that the EPV value manifests some drift with time, according to which a measured EPV value, having no specified component(s) from the sample gas/fluid present, will not remain constant but will change or drift with time. For one class of models, the difference, $\Delta$EPV(t;q;meas)=EPV(t;q;meas)−EPV(t=0; meas), is of primary importance. For another class of models the compensated value EPV(t;q;comp)=EPV(t;q;meas)= EPV(t;q;base) is of primary importance.

In a preferred embodiment, for each specified component $SC_m$, and each different sensor (numbered q=1, . . . , Q), a set of reference electrical parameter values $\Delta$EPV(($SC_m$;r), q;r) are measured for a set of reference concentrations $\kappa(SC_m;r)$. (r=1, . . . , R) of each specified component (m). Q EPV measurements $\Delta$EPV(pat;q) are also provided (q=1, . . . , Q) for the patient.

The electrical parameter values ("EPVs"), comprise electrical current, voltage difference, resistance, impedance, conductance or capacitance. An EPV change value $\Delta$EPV may be positive or negative, depending upon interaction between the specified component and the functionalized NS. Each NS in a sub-array is connected at its first end and second end to first and second electrodes, respectively, and a $\Delta$EPV measurement mechanism is also connected between the first and second electrodes. The method and system can be used to test other types of samples, such as headspace of a sample of urine or blood and aromas from the skin or from an ear.

In a first procedure, pattern recognition or discrimination is implemented by comparing magnitudes of differences of normalized $\Delta$EPV values for the reference set and for the patient, summed over the different sensors for each of the specified components $SC_m$. For each of these sums that is no greater than a threshold number, which may depend upon the specified component $SC_m$, the system interprets this condition as indicating that this specified component is likely present in a substantial or non-negligible concentration in the patient's sample gas (a "surviving" subset of specified components).

For a sum that is greater than the corresponding threshold number, the system optionally interprets this condition as indicating that this specified component is likely present, if at all, in a negligible concentration in the patient's sample gas.

The specified components that survive this comparison process are then subjected to a second procedure. Calibration parameters are estimated, relating a polynomial of concentration values κ for a fixed, surviving specified component to each of the reference set of ΔEPV values. A second sum of magnitudes of differences between the patient's ΔEPV values, suitably weighted, and the calibrated ΔEPV values for the surviving specified components, summed over the different sensors is provided. An optimum numerical value of this non-negative "suitable weight" is expressed as a linear or quadratic polynomial in the concentration value κ that minimizes the second sum, and this optimum combination is used to estimate the concentration value of each of the surviving specified components in the sample gas.

The first procedure identifies specified components that are present in non-negligible concentrations in the patient's sample gas. The second procedure uses a polynomial approximation to estimate concentration values for surviving specified components in the patient's sample gas and identifies which of these estimates may be reasonably accurate. The estimated concentration values for the surviving component(s) are used to estimate whether a disease D may be present.

DESCRIPTION OF THE INVENTION

Figure 2:
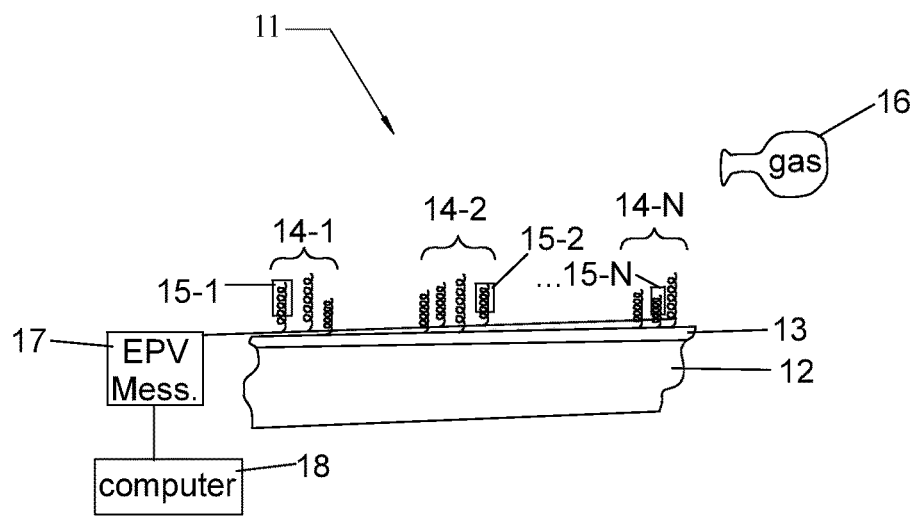
FIG. 2 illustrates a system, including an array of functionalized NSs connected through first and second electrodes to EPV measurement mechanisms.

FIG. 2 schematically illustrates a measurement system 21 for practicing the invention. The measurement system 21 includes: a substrate 22; an appropriate catalyst underlayer 23 (optional); a sequence of distinct sub-arrays 24-$q$ (q=1, ..., Q; Q≥2) of nanostructures ("NSs") grown or deposited on the substrate; a selected "loading" (e.g., doping, impregnation, coating, non-functionalized) 25-$q$ of the NS sub-array 24-$q$; a source 26 of a "sample gas" (e.g., breath or urine of a patient or test subject) to be interrogated; an EPV measurement mechanism 27 for measuring an electrical parameter change value, ΔEPV(t;q;meas) at each of the Q NS sub-arrays, before and after exposure of that sub-array to the sample gas; a computer or smart phone or computerized tablet 28 (referred to collectively herein as a "computer"), programmed: to receive the sequence of measured electrical parameter values ΔEPV(q;meas;t) or change values ΔEPV(t;q;meas), to compare the measured value ΔEPV(q;meas) with corresponding reference values ΔEPV (q;ref), and to estimate whether a specified chemical component is likely present in the sample gas, a most probable concentration value (if the specified component is likely present, a phone network 29, and a solid state system refresh mechanism 30 (optional), to refresh and reset the NS sub-arrays for a subsequent measurement. Each NS sub-array 24-$q$ may consist of a single NS or may include two or more NSs with the same substrate material and the same functionalization. Two different NS sub-arrays, 24-$q$ (q=q1, q2), may have the same number, or different numbers, of NSs. For some sample gases, the response time for detection is no more than 2 sec; and the minimum detection value for some substances appear to be below 5 ppb (e.g., $NO_2$, with an estimated detection limit of about 4.6 ppb at T=25° C.). Response time for detection of other gases may be higher and/or the detection limit (minimum concentration value) may have a larger value. After the measurements and analyses are performed, the results and conclusions are displayed and/or distributed by an information distribution system, such as a digital cell phone or a digital phone network.

Up to 32 individually functionalized NS channels were initially tested and confirmed to work as expected. This number has been increased to 64 channels (1 cm×1 cm size), and will be increased further as the perceived need increases, up to 256 channels. An array of 32 NS channels, integrated with a sampling system and associated electronics, has been reduced to postage stamp size, which can fit into, and provide connections to, a cell phone or smart phone with which the sensor array is integrated.

The area density per unit mass for the NS is very high, about 1600 $m^2$/gm in one embodiment, so that an EPV change value ΔEPV is quite sensitive to presence of even a small amount of a sample gas. For example, presence of nitrogen dioxide ($NO_2$) at a concentration of 4.6 parts per billion (ppb) has been detected using one NS array. With an appropriate choice of differently functionalized NSs, the NS sub-array can collectively distinguish between presence of at least two different sample gas components and allow an estimate to be made of most probable concentration value for each component, above a detection threshold concentration. Thus far, I have tested the functionalized NS sub-array on about ten different gases, including nitrous oxide (NO), hydrogen peroxide ($H_2O_2$), carbon dioxide ($CO_2$), hydrogen chloride (HCl), ammonia ($NH_3$), chlorine ($Cl_2$), formaldehyde ($CH_2O$), acetone ($CH_3COCH_3$), isopropyl alcohol (($CH_3)_2CHOH$), methane ($CH_4$), benzene ($C_6H_6$), and sulfur dioxide ($SO_2$).

Of course, as the number of different specified components tested for presence increases, the required number of separately functionalized NSs also increases. The sensors constructed using the functionalized NSs are robust, long lasting (at least three years lifetime), and will operate in the presence of high intensity vibrations, and the measured values can be compensated for varying ambient temperature, varying ambient humidity and varying ambient pressure.

An NS sub-array can be recycled or refreshed, after its use for a particular chemical component, by at least two methods: (1) local heating of the NS sub-array with energy density of the order of 1-100 Joules/$cm^2$ for 10-30 sec and (2) irradiation of the NS sub-array with ultraviolet-emitting LEDs (e.g., with wavelengths in a range (e.g., 254-256 nm) for 1-100 seconds.

The particular electrical parameter change value ΔEPV(t; q;meas), measured for each of the functionalized sensor sub-arrays, may be electrical impedance, resistance, conductance, capacitance, inductance, electrical voltage, electrical current, or some other relevant, measurable electrical value. For electrical current, for example, the change values ΔEPV(t;q;meas) are often measured in μAmps or in mAmps; for resistance, the change value ΔEPV(t;q;meas) (possibly dependent upon time t) are often measured in tens of Ohms, up to several kilo-Ohms.

In a pattern recognition approach adopted here, the pattern is provided by a sequence of combined analytical and empirical relations, with one such relation for each of Q distinct combinations of sensor materials and functionalization processes, and with a least-pth-power analytical procedure for estimating most-probable concentrations values of specified components.

Figure 3A:
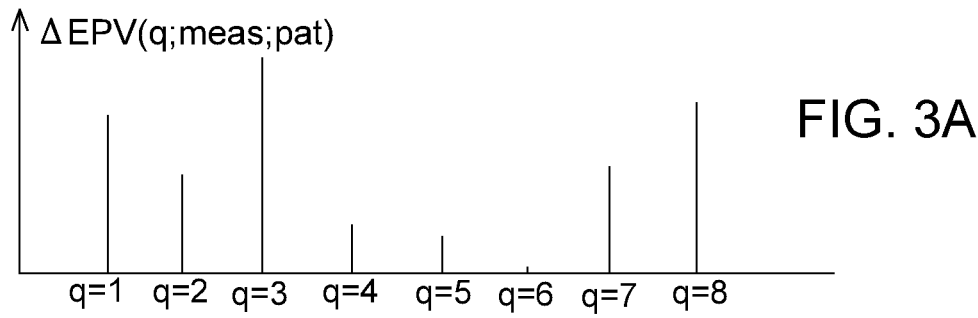
FIGS. 3A-3E are graphs used in a method for practicing an embodiment.
Figure 3B:
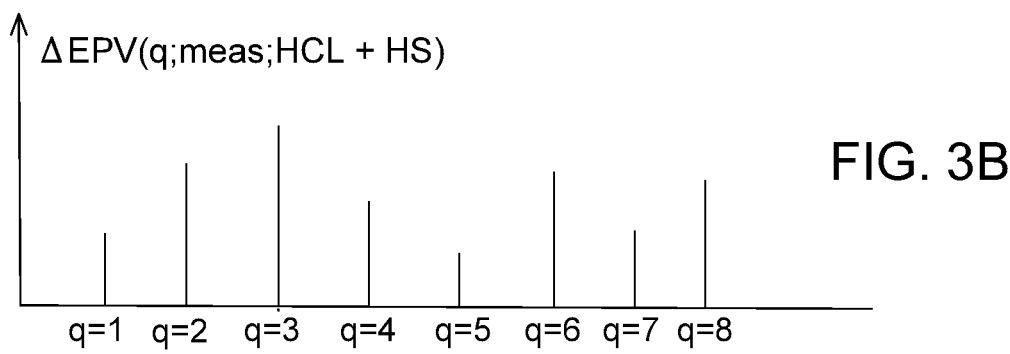
Figure 3C:
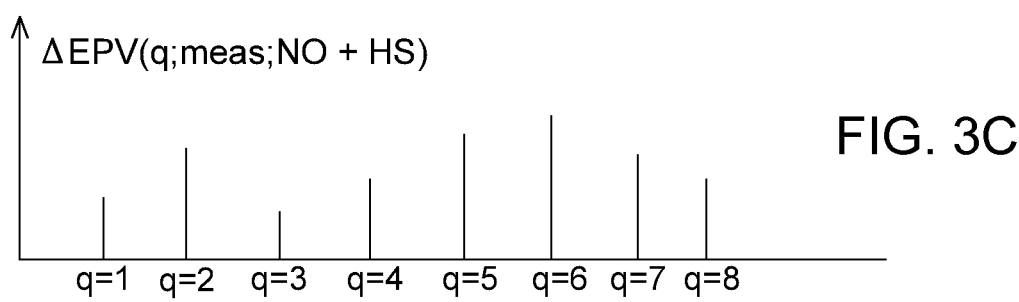
Figure 3D:
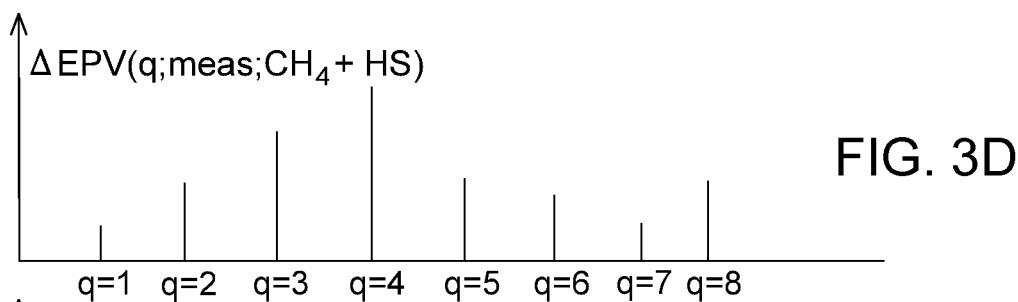
Figure 3E:
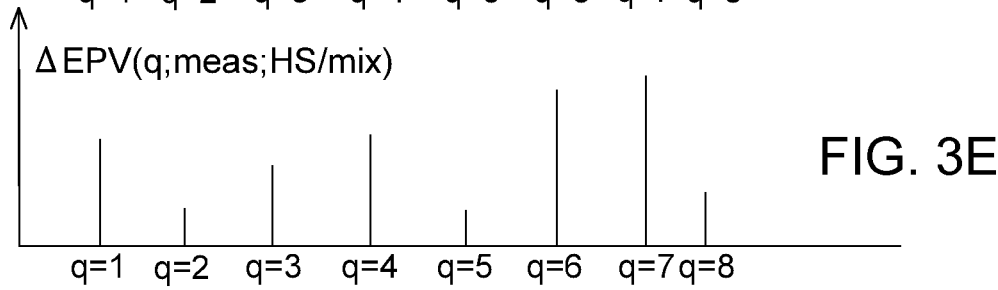
Figure 4A:
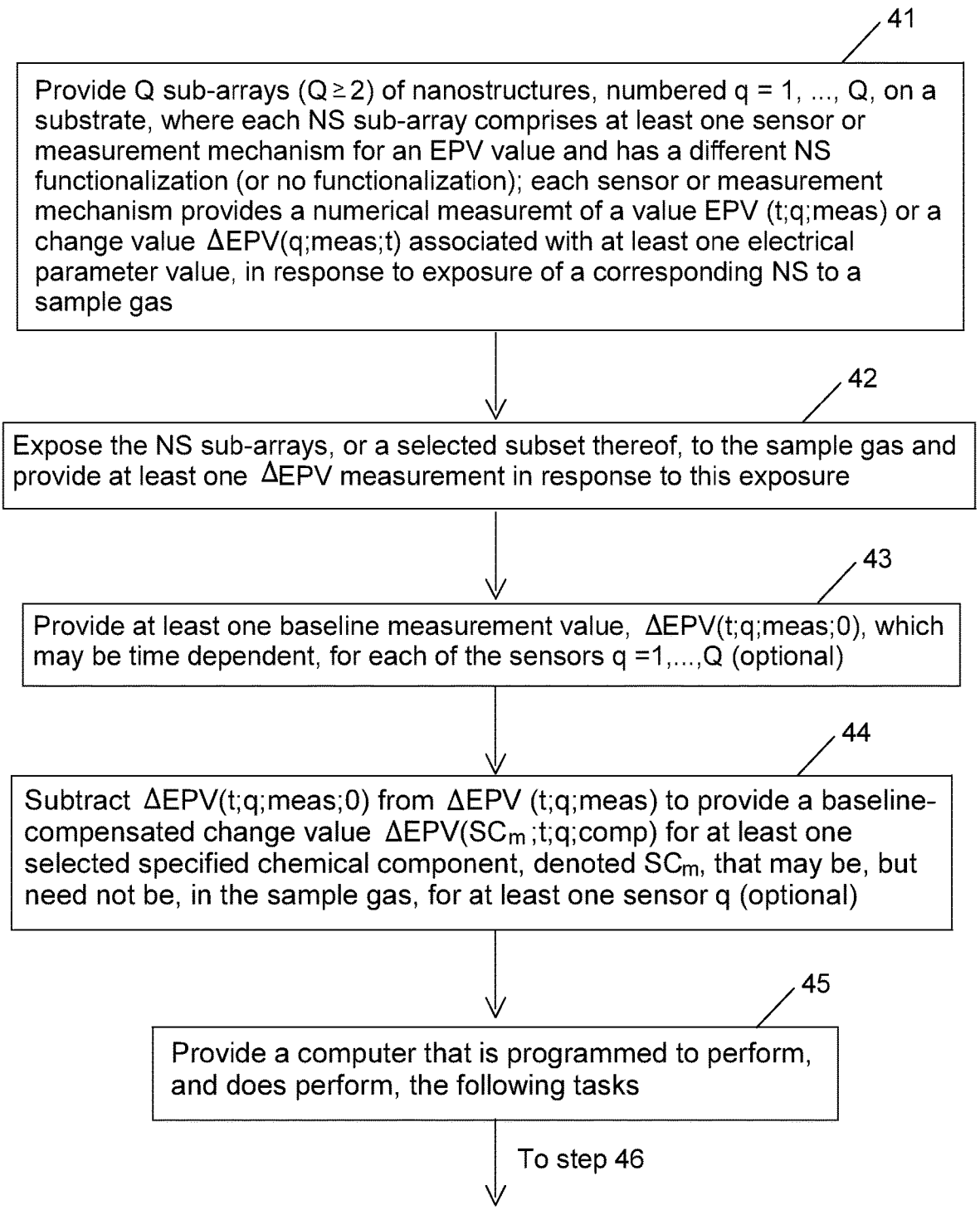
FIGS. 4A-4D are a flow chart of a method for practicing an embodiment.
Figure 4B:
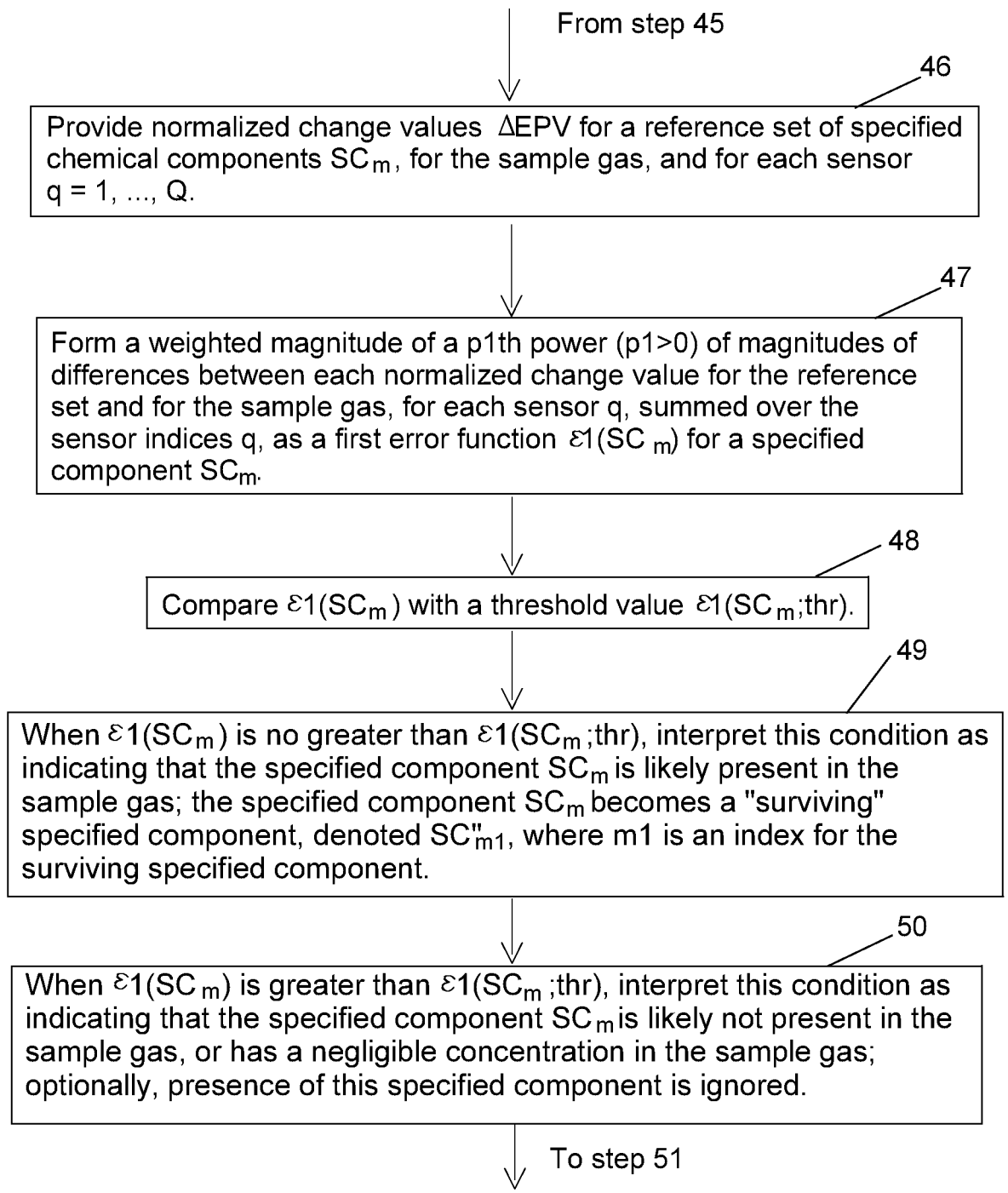
Figure 4C:
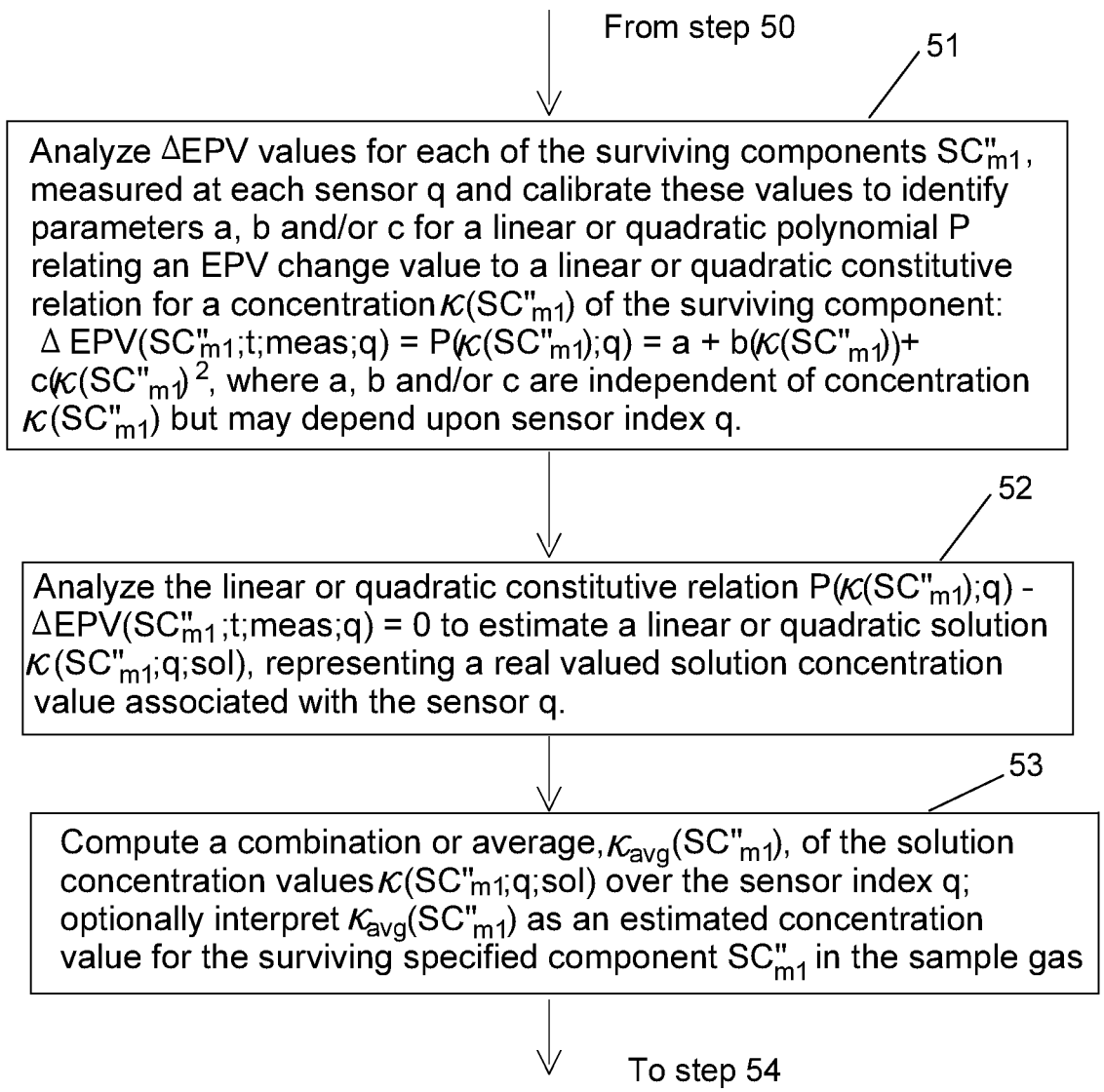
Figure 4D:
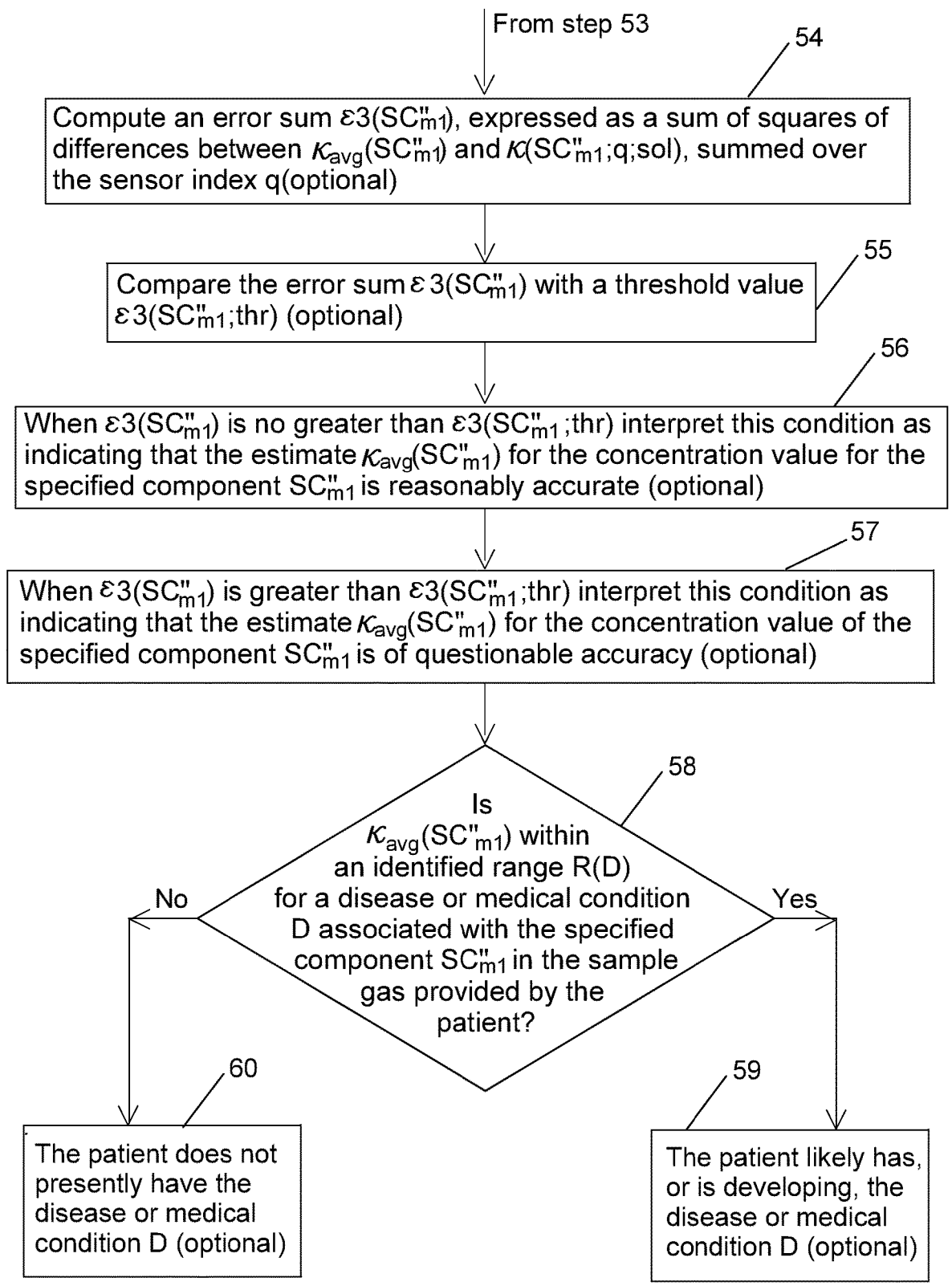

FIGS. 3A-3E are graphs of ΔEPV amplitudes for Q distinct sensors, numbered q=1, ..., Q (Q≥2; Q=8 here), from: (1) a sample gas measured from the patient (FIG. 3A); a first reference sample having a known concentration of HCl plus HS gas (FIG. 3B), a second reference having a known concentration of NO plus HS gas (FIG. 3C), a third reference sample having a known concentration of $CH_4$ plus HS gas (FIG. 3D); and gas from one or a mixture of persons (not including the patient) that are known to have none of the diseases associated with the specified compound. The Q sensors are distinguishable by use of different sensing materials (metals, semiconductors, polymers, carbon-based nanostructures, etc.) and/or by use of different functionalization processes. FIG. 3E illustrates ΔEPV amplitudes for the Q sensors for a representative ambient gas.

Amplitudes A(SC;q) of the measured values, ΔEPV($SC_m$;q), are presented on a graph or otherwise provided for each of M specified components ($SC_m$), with each of the sensor materials set forth on the graph.

A set of reference samples of measured ΔEPV values is provided, with each sample initially including the HS gas. Each of a sequence of selected concentration values κ($SC_m$;r), (e.g., 1 ppm, 5 ppm, 10 ppm, 25 ppm; corresponding to r=1, ..., R) of a fixed specified compound is added to the initial reference healthy sample (HS) gas, to form a reference test sample. Each of the sensors is exposed to each of the reference test samples, and an EPV value is measured and recorded. The change value ΔEPV occurs in response to exposure to the sample gas, corresponding to one sensor, to (dominating) presence of only one specified compound present at a known concentration value, κ($SC_m$;r), and to presence of only one reference concentration (r) of the specified chemical component.

A first procedure determines whether a given specified component ($SC_m$), is present in the sample gas measured from the patient. Normalized amplitudes $A_n$ are first formed for the reference amplitudes A($SC_m$,q) and for the measurements for the patient, defined as $$A_n(SC_m, q) = \frac{A(SC_m, q)}{\text{Sum}(SC_m)}, \quad (1)$$

$$A_n(pat, q) = \frac{A(pat, q)}{\text{Sum}(pat)}, \quad (2)$$

$$\text{Sum}(SC_m) = \sum_{q=1}^{Q} A(SC_m, q), \quad (3)$$

$$\text{Sum}(pat) = \sum_{q=1}^{Q} A(pat, q). \quad (4)$$

For each specified component $SC_m$, a first error function $$\varepsilon1(SC_m) = \sum_{q=1}^{Q} u_q |A_n(SC_m, q) - A_n(pat, q)| \quad (5)$$

is computed, where p is a chosen positive exponent value and the weight parameters $u_q$ are non-negative and may be chosen to satisfy $$\sum_{q=1}^{Q} u_q = 1, \quad (6)$$

For computational convenience, the exponent parameter p may be chosen to be p=2, and/or the weights $u_q$ may be uniform ($u_q$=1/Q)

The numerical value of the first error function ε1($SC_m$) is compared with a first threshold value ε1($SC_m$;thr), which may vary from one specified component to the next. When ε1($SC_m$) is no greater than ε1($SC_m$;thr), the system interprets this condition as indicating that the specified component $SC_m$ is likely present in the sample gas. The surviving specified components, which satisfy this condition, are denoted $SC''_{m1}$, where m1 is an index of surviving specified components.

When ε1($SC_m$) is greater than ε1($SC_m$;thr), the system interprets this condition as indicating that the specified component $SC_m$ is likely (i) not present in the sample gas or (ii) present in the sample gas with a negligible concentration κ($SC_m$) of the specified component, whose presence can be optionally ignored. One or more specified components $SC_m$ may not survive this comparison process and are optionally discarded in the subsequent analysis.

A second procedure provides an estimate of concentration κ($SC''_{m1}$), of the surviving specified components in the sample gas. Each of the graphs in FIGS. 3B, 3C and 3D provides normalized samples over R=2, 3 or more concentration values κ($SC''_{m1}$), for the surviving specified component $SC''_{m1}$ indicated in the graph. The EPV value may be represented by a linear or quadratic relation between ΔEPV and concentration κ($SC''_{m1}$), for that surviving SC, $$\Delta EPV(\text{approx}) = a + b\kappa(SC''_{m1}) + c\kappa(SC''_{m1})^2, \quad (7)$$

where a, b and c are parameters, possibly dependent upon $SC''_{m1}$ and/or q and independent of concentration values κ($SC''_{m1}$), to be determined separately for each sensor q and for each surviving specified compound $SC''_{m1}$, and a is the ΔEPV value, measured for that sensor, where only an HS gas is present. For a fixed specified component $SC''_{m1}$, with varying concentration values κ($SC''_{m1}$r) (r=1, ..., R; R≥2), a collection of two, three or more measurement pairs (κ($SC''_{m1}$;q;r), EPV($SC''_{m1}$;r) is assembled, for different SC concentrations, indexed by r.

In one approach, the parameters a, b and c are estimated by minimizing a second error function $$\varepsilon2(SC''_{m1}; q; a; b; c) = \quad (8)$$

$$\sum_{r=1}^{R} \{a + b\kappa(SC''_{m1}; r) + c\kappa(SC''_{m1}; r)^2 - \Delta EPV(SC''_{m1}; q; r; ref)\}^2$$

with respect to the parameters a, b; and c; (quadratic relationship), or with respect to the parameters a and b (linear relationship). This can be done by setting the partial derivative of ε2 with respect to the corresponding parameter (a, b or c) equal to 0. The result of these minimizations is a coupled set of equations:

$$Aa+Bb=C, \quad (9)$$

$$Da+Eb=F, \quad (10)$$

$$A = \sum_{r=1}^{R} \{1\}, \quad (11)$$

$$B = \sum_{r=1}^{R} \kappa(SC''_{m1}; r) = D, \quad (12)$$

$$E = \sum_{r=1}^{R} \kappa(SC''_{m1}; r)^2, \quad (13)$$

$$C = \sum_{r=1}^{R} \Delta EPV(SC''_{m1}; q; r; ref), \quad (14)$$

$$F = \sum_{r=1}^{R} \Delta EPV(SC''_{m1}; q; r; ref)\kappa(SC''_{m1}; r), \quad (15)$$

for a linear relationship. For a quadratic relationship, Eqs. (16)-(26) are used.

$$Ga'+Hb'+Jc'=K, \quad (16)$$

$$La'+Mb'+Nc'=P, \quad (17)$$

$$Ra'+Sb'+Tc'=U, \quad (18)$$

$$G = \sum_{r=1}^{R} \{1\}, \quad (19)$$

$$H = \sum_{r=1}^{R} \kappa(SC''_{m1}; r) = L, \quad (20)$$

$$J = \sum_{r=1}^{R} \kappa(SC''_{m1}; r)^2 = M = R, \quad (21)$$

$$N = \sum_{r=1}^{R} \kappa(SC''_{m1}; r)^3 = S, \quad (22)$$

$$T = \sum_{r=1}^{R} \kappa(SC''_{m1}; r)^4, \quad (23)$$

$$K = \sum_{r=1}^{R} \Delta EPV(SC''_{m1}; q; r; ref), \quad (24)$$

$$P = \sum_{r=1}^{R} \Delta EPV(SC''_{m1}; q; r; ref)\kappa(SC''_{m1}; r), \quad (25)$$

$$U = \sum_{r=1}^{R} \Delta EPV(SC''_{m1}; q; r; ref)\kappa(SC''_{m1}; r)^2 \quad (26)$$

Solution of the relations (9) and (10), or (16), (17) and (18) is straightforward, using algebraic maneuvers, such as Cramer's rule.

The preceding linear or quadratic relationships are applied separately for each surviving specified component $SC''_{m1}$, for different SC concentrations $r=1, \ldots, R$; and for each sensor q; only one surviving SC is considered at a time. For purposes of this discussion, the linear relation (c=0) or the quadratic relation between $\Delta EPV$ value and SC concentration values can be applied.

The amplitudes for the $\Delta EPV$ values, denoted $A(SC''_{m1}; q)$, for the Q distinct sensors for the surviving specified compounds $SC''_{m1}$=HCl, NO and $CH_4$, are shown as examples in FIGS. 3B, 3C and 3D, where each SC in each of these Figures corresponds to a known concentration, $\kappa(HCl)$, $\kappa(NO)$ and $\kappa(CH_4)$, respectively, which need not be the same for each component. A higher amplitude for a given SC indicates a higher sensitivity of the corresponding sensor material to presence of that component $SC''_{m1}$ with a known concentration $\kappa(SC''_m;r)$. For each surviving specified component $SC''_{m1}$, the measured EPV changes values $\Delta EPV(SC''_{m1},pat;q)$ for the patient for each sensor q are used to estimate an associated concentration value as a solution of a linear equation in $\kappa(SC''_{m1};q)$, $$a'+b'\kappa(SC''_{m1};q)=\Delta EPV(SC''_{m1};q), \quad (27)$$

or as a solution of a quadratic equation $$a'+b'\kappa(SC''_{m1};q)+c'\kappa(SC''_{m1};q)^2=\Delta EPV(SC''_{m1};q), \quad (28)$$

depending upon one's choice of the constitutive relation, Eq. (7), that is used. The associated solutions $\kappa(SC''_{m1};q;sol)$, for a fixed $SC''_{m1}$ and varying q, will not be identical but may be reasonably close to each other.

A selected combination or statistical average $\kappa_{avg}(SC''_{m1})$ (preferably symmetric in the solution values) is computed for the solution concentration values $\kappa(SC''_{m1};q;sol)$ over the sensors, $q=1, \ldots, Q$. One suitable average is an arithmetic average $$\kappa_{avg}(SC''_m) = \frac{1}{q}\sum_{q=1}^{Q} \kappa(SC''; q; sol), \quad (29)$$

Another suitable average is a geometric average, formed as a 1/Q power of a finite product of the Q solution concentration values $$\kappa_{avg}(SC''_m) = \sqrt[Q]{\prod_{q=1}^{\Theta} \kappa(SC''; q; sol)}, \quad (30)$$

where it is assumed that none of the solution concentration values $\kappa(SC'';q;sol)$ is zero or near zero for this surviving specified component $SC''_{m1}$. Other averages, symmetric or otherwise, can also be used here. The combination $\kappa_{avg}(SC''_m)$ is interpreted as a probable concentration value for the surviving specified component $SC''_{m1}$ in the sample gas.

A Third Error Function $$\varepsilon3(SC''_{m1}) = \sum_{q=1}^{Q} (\kappa(SC''; q; sol) - \kappa_{avg}(SC''_{m1}))^2, \quad (31)$$

is formed from a square of differences between the combinations or averages $\kappa_{avg}(SC''_{m1})$ and the solution concentration values $\kappa(SC''_{m1};q;sol)$. The third error function $\varepsilon3$ is a measure of standard deviation (SD) relative to a statistically averaged value $\kappa_{avg}(SC''_{m1})$.

The error value $\varepsilon3(SC''_{m1})$ may be compared with a threshold value $\varepsilon3(SC''_{m1};thr)$. When $\varepsilon3(SC''_{m1})$ is no greater than $\varepsilon3(SC''_{m1};thr)$, the system interprets this condition as indicating that the combination K estimate for $avg(SC''_{m1})$ estimate for the concentration value(s) $\kappa(SC''_{m1})$ is reasonably accurate and can be used as an estimate for the concentration value $\kappa(SC''_{m1};pat)$ of the surviving specified component $SC''_{m1}$ in the sample gas.

When $\varepsilon3(SC''_{m1})$ is greater than $\varepsilon3(SC''_{m};thr)$, the system optionally interprets this condition as indicating that this average $\kappa_{avg}(SC''_{m1})$ of the solution concentration values $\kappa(SC''_{m1};q;sol)$ has questionable accuracy.

Figure 1:
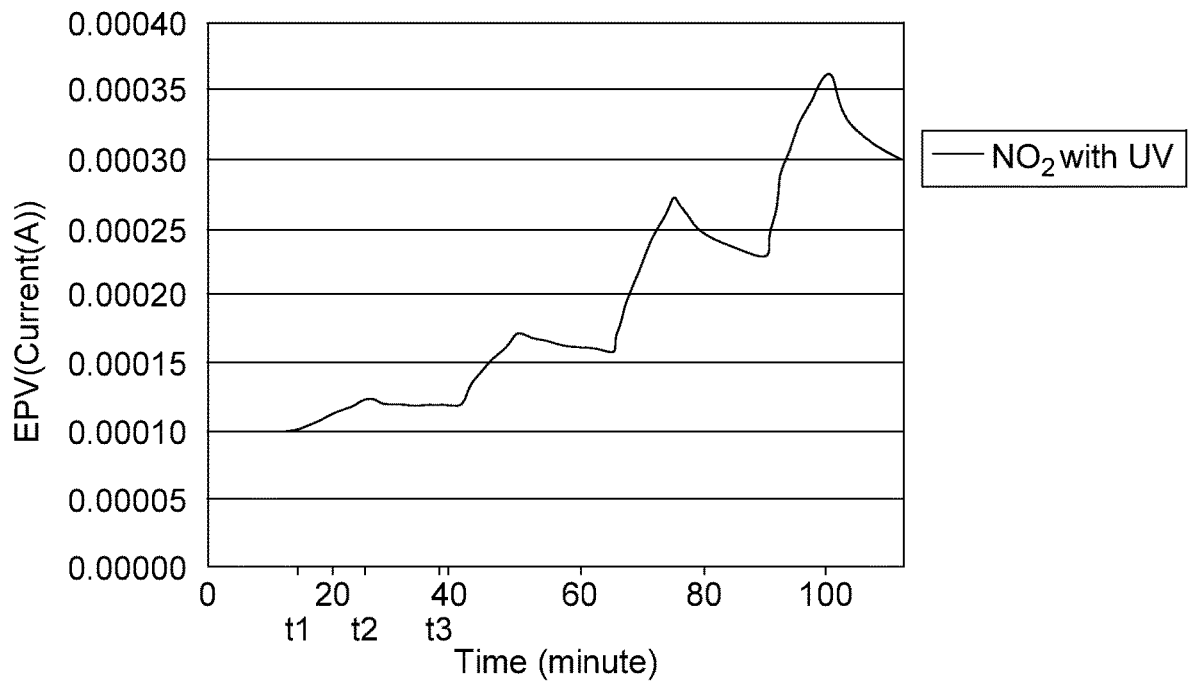
FIG. 1 graphically illustrates time variation of some useful electrical parameter value

Optionally, a baseline measurement, denoted $\Delta EPV(t;q;0)$ and shown in FIGS. 1 and 3E (HS gas), is also made for each of the Q distinct sensors, where only an HS gas is present. The baseline value $\Delta EPV(t;q;0)$, which may be time dependent, is subtracted from the measured change value $\Delta EPV(t;q;meas)$ to provide a baseline-compensated value $$\Delta EPV(t;q;comp) = \Delta EPV(t;q;meas) - \Delta EPV(t;q;0) \tag{32}$$

for a particular SC and for a particular sensor or NS number q.

FIGS. 4A-4D are a flow chart of a procedure for practicing an embodiment of the invention. In step 41, Q sub-arrays of nanostructure (NS) sub-arrays (Q>1) are provided on a substrate, where each NS sub-array comprises at least one sensor or measurement mechanism for an EPV value and has a different NS functionalization (or no functionalization). Each sensor comprises at least first and second interdigitated electrodes, with each electrode being connected at a first electrode end to at least one of (i) a controllable voltage source and (ii) a controllable current source and the first and second ends of an electrode being connected to each other in an electrical path that includes one or more of the functionalized (or non-functionalized) nanostructures. Each sensor or measurement mechanism provides a numerical measurement associated with a change in an electrical parameter value $\Delta EPV$ (t;q;meas), representing a change in at least one of electrical voltage difference, electrical current, impedance, resistance, conductance, inductance or another relevant EPV value, in response to exposure of a corresponding NS to a sample gas.

In step 42, the NS sub-arrays, or a selected subset thereof, are exposed to the sample gas and at least one $\Delta EPV$ measurement is provided in response to this exposure. In step 43 (optional), at least one baseline measurement $\Delta EPV$, denoted $\Delta EPV$ (t;q;meas;0), which may be time dependent, is provided for at least one measurement time value t. In step 44 (optional), a baseline measurement $\Delta EPV$ (t;q;meas;0) is subtracted from a $\Delta EPV$ measurement value to provide a baseline-compensated $\Delta EPV$ value $\Delta EPV(t;q;meas;base)$, which may depend, but need not depend, upon a time value t.

In step 43 (optional), a baseline $\Delta EPV$ measurement, denoted $\Delta EPV(t;q;0)$ (HS gas), is also made for each of the Q distinct sensors, where only an HS gas is present. In step 44 (optional), the baseline change value $\Delta EPV(t;q;0)$, which may be time dependent, is subtracted from the measured change value $\Delta EPV$ to provide a baseline-compensated change value $\Delta EPV(SC''_{m1};t;q;comp)$ for a particular SC and for at least one sensor q, as illustrated in FIG. 1.

A computer is provided that is programmed to perform, and does perform, the following tasks, in step 45.

In step 46, normalized change values $\Delta EPV$ for a reference set of specified chemical components $SC_m$ and for the sample gas are formed, as set forth in Eqs. (1)-(4). In step 46, for each specified component $SC_m$, (a candidate for inclusion in the sample gas) and for each sensor q, a first error function $\varepsilon1(SC_m)$ is formed as a pth power of weighted magnitudes of differences between the normalized change values for the reference set and for the sample gas, and these weighted differences are summed over the sensors, $q=1, \ldots, Q$, as set forth in Eq. (5), where the weighting parameters $u_q$ are non-negative and the sum of the weighting parameters over the Q sensors is equal to a positive constant (e.g., 1). In step 48, the numerical value of the first error function $\varepsilon1(SC_m)$ is compared with a first threshold value $\varepsilon1(SC_m;thr)$, which may vary, but need not vary, with the specified component.

When $\varepsilon1(SC_{m1})$ is no greater than $\varepsilon1(SC_m;thr)$, the system interprets this condition as indicating that the specified component $SC_m$ is likely present in the sample gas, in step 49. A first subset of specified components $SC_m$ that satisfy the condition in step 48 become a surviving subset of specified components, $\{SC''_{m1}\}$, where m1 is an index for this first subset.

When $\varepsilon1(SC''_m)$ is greater than $\varepsilon1(SC_m;thr)$, the system interprets this condition as indicating that the specified component $SC_m$ likely (i) is not present in the sample gas or (ii) is present in the sample gas with a negligible concentration $\kappa(SC_m;pat)$, in step 50; and presence of this second subset of specified components in the sample gas is optionally ignored.

In step 51, each of the set of surviving specified components $SC''_{m1}$, measured at each sensor q, is analyzed or calibrated as in Eqs. (9)-(26), using known concentrations (indexed by r) of the surviving components with their measured change values $\Delta EPV(\kappa(SC''_{m1};q;r))$, to identify parameters a, b and/or c, for which a linear polynomial approximation $$\Delta EPV(SC''_m;q;approx) = a + b\kappa(SC''_m), \tag{33A}$$

or a quadratic polynomial approximation $$\Delta EPV(\kappa(SC''_{m1};q;approx)) = a + b\kappa(SC''_m) + c\kappa(SC''_{m1})^2, \tag{33B}$$

provides a best linear fit or a best quadratic fit, respectively, for a fixed surviving specified component $SC''_{m1}$, and a fixed sensor q, for the reference set of concentration values $(r=1, \ldots, R)$. The parameters a, b and c are independent of concentration values $\kappa(SC''_m;r)$ but may depend upon the choice of surviving specified compound $SC''_{m1}$; and/or upon the choice of sensor q.

In step 52, a linear constitutive relation, $$a' + b'\kappa(SC''_{m1};q) - \Delta EPV(SC''_{m1};q) = 0, \tag{34A}$$

or a quadratic constitutive relation, $$a' + b'\kappa(SC''_m;q) + c'\kappa(SC''_m;q)^2 - \Delta EPV(SC''_{m1};q) = 0, \tag{34B}$$

is analyzed to estimate a solution concentration value $\kappa(SC''_{m1};q;sol)$ as a real valued solution for Eq. (34A) or Eq. (34B) for each surviving specified component $SC''_{m1}$ and for each NS number q ($q=1, \ldots, Q$) In step 53, a combination or average, $\kappa_{avg}(SC''_{m1})$ is computed, representing an average, of the solution concentration values $\kappa(SC''_m;q;sol)$, over the index q, for example as set forth in Eq. (29) or (30), is formed. The corresponding value $\kappa_{avg}(SC''_{m1})$ is optionally interpreted as an estimated concentration value for the surviving specified component $SC''_{m1}$ in the sample gas.

In step 54 (optional), a sum of a square of differences between $\kappa_{avg}(SC''_{m1})$ and each of the sum of solution concentration values $\kappa(SC'';q;sol)$ is formed, and an error sum $\varepsilon3(SC''_{m1})$, over the sensor index q is computed.

In step 55 (optional), the error sum $\varepsilon3(SC''_{m1})$ is compared with a threshold value $\varepsilon3(SC''_{m1};thr)$. When $\varepsilon3(SC''_{m1})$ is no greater than $\varepsilon3(SC''_{m1};thr)$, the system interprets this condition as indicating that the estimate $\kappa_{avg}(SC''_{m1})$ for the concentration value for the surviving specified component $SC''_{m1}$ in the sample gas is reasonably accurate, in step 56 (optional). When $\epsilon3(SC''_{m1})$ is greater than $\epsilon3(SC''_{m1};thr)$, the system interprets this condition as indicating that the estimate $\kappa_{avg}(SC''_{m1})$ for the concentration value for the surviving specified component $SC''_{m1}$ in the sample gas has questionable accuracy, in step 57 (optional). In step 58, the system determines whether $\kappa_{avg}(SC''_{m1})$ is within an identified range R(D) for a disease or medical condition D that is associated with presence of the surviving specified component $SC''_{m1}$ in the sample gas provided by the patient.

When the question in step 58 is answered affirmatively, the system interprets this condition as indicating that the patient is likely to have, or to be developing, the disease D or medical condition, in step 59 (optional). When the question in step 58 is answered negatively, the system interprets this condition as indicating that the disease or medical condition D is not likely present in the patient, in step 60 (optional). Steps 58, 59, 60 can be applied to a disease D for which a range R(D) of concentration values $\kappa(SC''_{m1})$ can be identified. Some ranges can be identified in the Tables 1, 2 and 3.

The materials used for constructing the sensors used here include carbon nanotubes (CNTs), including single wall and multiple wall, and CNTs with nanoparticles. The functionalization processes used here include doping with Pt and/or Pd.

Optionally, the invention includes a smart phone, cell phone tablet or similar communications system, indicated as 29 in FIG. 2, that can be used to transmit data and/or metadata concerning estimated concentration(s) of one or more surviving specified components to a physician, health clinic or other processor or repository of such information.

Several groups of researchers have reported relationships, and quantitative results, between selected diseases and detection of particular chemical compounds in a patient's breath, urine, blood and/or other essences from a patient's skin or ear (referred to collectively as "aromas of the body"). Breath biomarkers associated with six identified diseases or disease groups (oxidative stress, metabolic disorders, gastrocentric, exposure to volatile organic compounds, respiratory disorders, and renal failure) are reported by W. Cao and Y. Dunn (Clinical Chemistry, vol. 52:5 (2006) pp 800-811)) and are summarized in Table 1. The oxidative stress disorders include lipid peroxidase, asthma, COPD (several varieties), cystic fibrosis, pulmonary allograft, lung cancer and acute lung transplant rejection. Metabolic disorders include diabetes, gastroenteric diseases include Helicobacter pylori and imbalance of acid-base, Na, K, Ca, P, H, Mg or ketone. Respiratory disorders include ARDS. The biomarker compounds include NO (at least 15 ppb for asthma), $CO_2$, $H_2O_2$, ethane, pentane, isopentane, mono-ethylated alkanes, nitrite/nitrate ratio, acetone (normal is around 300 ppb), other ketones, carbonyl sulfate, vinyl chlorides and urine smell.

V. Salomas, et al, Open Access, 9 Apr. 2010, *PLOS ONE*, report on association of breath biomarkers with particular diseases and/or medical conditions; this work is summarized in Table 2. The top associations differ by gender (adult male versus adult female), with some overlap. Adiponectin, apoliprotein B and C-reactive protein (CRP) are the biomarkers with the first, second and third strongest associations, with diabetes and obesity, with obesity, and with future diabetes, respectively. Ferritin and Interleukin are the biomarkers with the fourth and fifth strongest disease associations for adult males, and Insulin is the biomarker with the fourth strongest association for adult females.

Breath biomarker versus disease associations are also reported by W. Miekisch, et al (Clinical Chemistry, vol 47:6 (2001) pp. 1053-1060) and are summarized in Table 3. The breath biomarkers acetone (normal is about 300 ppb), n-pentane (3.5 nmol/L recovery), isoprene (10.5 nmol/L recovery), isoflurane and dimethyl sulfide are associated with diabetes mellitus, lipid peroxidase, acute lung injury or dysfunction, liver disease or dysfunction (3.9 nmol/L recovery).

A $\Delta EPV$ value associated with an aroma or a liquid composition from a patient's urine or a patient's blood can also be used to evaluate whether a particular disease D or medical condition is present. For diabetes, type 1 or type 2, the sample gas is the patient's breath, the surviving specified chemical component $SC''_{m1}$ is acetone, and the threshold concentration $\kappa(SC''_{m1};thr)$ (lower bound) may be taken as 400, 500 or 600 ppb. For asthma, the sample gas is the patient's breath, the surviving specified chemical component $SC''_{m1}$ is NO, and the threshold concentration $\kappa(SC''_{m1};thr)$ (lower bound) may be taken as 20, 25 or 30 ppb. For acute lung injury, the sample gas is the patient's breath, the surviving specified chemical component $SC''_{m1}$ is isoprene, and the threshold concentration $\kappa(SC''_{m1};thr)$ (lower bound) may be taken as 12-15 nmol/liter or higher.

TABLE 1

Breath Biomarker/Disease Indicators (Cao/Duan).

| Indicator | Disease | Biomarker |
|---|---|---|
| Oxidative stress | Lipid peroxidase | pentane, ethane |
| | Asthma | NO (>15 ppb), $CO_2$, $H_2O_2$, isopentane, nitrite/nitrate ratio |
| | COPD | NO, $H_2O_2$, isopentane |
| | Cystic fibrosis | NO, $CO_2$, $H_2O_2$, isopentane, nitrite/nitrate ratio |
| | Pulmonary allograft | NO |
| | Lung cancer | NO, mono-methylated alkanes |
| | Lung transpl rejection | Carbonyl sulfide |
| Metabolic disorder | Diabetes | Acetone (normal is 300 ppb) |
| Gastroenteric disorder | | Acid-base, Na, K, Ca, P, Mg, abnormal H2, ketones |
| | H. pylori | $^{13}C$, $^{14}C$ isotopes (urea breath test) |
| Exposure to VOCs | | Vinyl chlorides |
| Respiratory disorder | ARDS | $O_2/CO_2$ ratio (inhaled/exhaled) |
| Renal failure | | Urine smell in breath |

TABLE 2

Breath Biomarker/Disease Indicator For Diabetes (Salomas, et al).

| Male subjects (NRI = 25.4%) | |
|---|---|
| Adiponectin | Correlation is inverse with diabetes and with obesity |
| Apoliprotein B | Assoc. with obesity? |
| C-reactive protein (CRP) | Assoc. with future diabetes |
| Ferritin | Significant for men only |
| Interleukin- 1ra | |
| Female subjects (NRI = 13.6%) | |
| Adiponectin | Correlation is inverse with diabetes and with obesity |

TABLE 2-continued

Breath Biomarker/Disease
Indicator For Diabetes (Salomas, et al).

| | |
|---|---|
| Apoliprotein B | Assoc. with obesity? |
| C-reactive protein (CRP) | Assoc. with future diabetes |
| Insulin | Significant for women only |

TABLE 3

Breath Biomarker/Disease Indicators (Miekisch, et al).

| Indicator | Disease | Remarks |
|---|---|---|
| Acetone | Diabetes mellitus | Normal conc is ≈ 300 ppb |
| n-pentane | Lipid peroxidization | Environ origin; septic patient → high conc; 3.5 nmol/L recovery |
| Isoprene | Acute lung injury | 10.5 nmol/L recovery |
| Isoflurane | | 4.6 nmol/L recovery |
| Dimethyl sulfide | Liver disease or dysf | Liver transplant → high conc; 3.9 nmol/L recovery |

Solution conc were 0.01-200 nmol/liter; 33 human patients plus 19 pigs examined

What is claimed is:

1. A system for medical diagnosis, the system comprising:
a plurality of nanostructure sensors disposed on one or more substrates, the plurality of nanostructure sensors comprising at least a first nanostructure sensor and a second nanostructure sensor, wherein each nanosensor is configured to provide a different sequence of electrical parameter values than another nanosensor of the plurality of nanosensors when exposed to a sample gas over a duration of time;
an analyzer system, comprising a processor and memory, configured to perform the following steps:
receiving a sequence of electrical parameter values measured from each nanostructure sensor of the plurality of nanosensors, each of the sequences corresponding to measured electrical values from a measurement mechanism;
generating a normalized amplitude value for one of the measured electrical values measured from each of the plurality of nanostructure sensors to form a set of amplitude values for the sample gas;
determining the presence of at least a first specified component in the sample gas by:
comparing a normalized amplitude value for the first nanostructure sensor for the sample gas with a reference amplitude value for the first nanostructure sensor for the first specified component to generate a compared value for the first nanostructure sensor;
repeating the comparing step for each of the other sensors of the plurality of nanostructure sensors to generate a set of the compared values;
aggregating the compared values to generated a set of aggregated compared values, wherein the aggregating includes a weighted summation of the compared values, and
based on the aggregated compared values, determining whether the specified component is likely present in the sample gas.

2. The system of claim 1, wherein at least the first nanostructure sensor is differently functionalized than and the second nanostructure sensor of the plurality of nanostructure sensors such that the first nanostructure sensor is differently sensitive to presence of a particular specified component than the second nanostructure sensor.

3. The system of claim 2, wherein at least the first nanostructure sensor and the second nanostructure sensor of the plurality of nanostructure sensors are functionalized by a functionalizing process comprising at least one of doping with Pt and doping with Pd.

4. The system of claim 1, wherein each of the nanostructure sensors is differently sensitive to at least two specified components.

5. The system of claim 1, wherein each value of the sequence of electrical parameter values for each nanostructure sensor is provided at various points over the duration of time.

6. The system of claim 1, wherein the one or more substrates comprise at least one of carbon nanostructures and carbon nanostructures that contain nanoparticles.

7. The system of claim 1, further comprising a measurement mechanism electrically coupled to each nanostructure sensor of the plurality of nanostructure sensors for measuring the electrical parameter values generated by each nanostructure sensor in response to exposure to the sample gas.

8. The system of claim 1, wherein the electrical parameter values includes one or more of electrical current, voltage difference, resistance, impedance, conductance and capacitance.

9. The system of claim 1, wherein the system comprises between 2 and 256 nanostructure sensors.

10. The system of claim 1, wherein the analyzer system is configured to identify presence two or more specified components after one exposure to the sample gas.

11. The system of claim 1, wherein the plurality of nanostructure sensors are refreshed by exposure to ultraviolet light from light-emitting diodes for a duration of 1 to 100 seconds.

12. The system of claim 1, wherein the step of determining whether the specified component is likely present in the sample gas includes the steps of:
generating an error value based on the aggregated compared values;
comparing the error value with a threshold error value; and
determining presence of the sample gas if the error value is less than the threshold error value.

13. The system of claim 1, wherein the sample gas is received from a patient.

14. The system of claim 1, the analyzer system further configured to perform the steps of:
analyzing a reference sample gas, the reference sample gas comprising a mixture of healthy sample gas having a known concentration of a specified component, the analyzing comprising determining two or more parameter values that associate the known concentration with a measured electrical value for the reference sample gas; and
determining a concentration of the specified component in the sample gas based on:
the set of measured electrical values for the sample gas, and
the two or more parameter values as determined in the analyzing the reference sample gas.

15. The system of claim 14, wherein the step of determining two or more parameter values that associate the known concentration with the measured electrical value includes determining at least one of a linear relationship or a quadratic relationship between the known concentration and the measured electrical value.

16. The system of claim 14, the analyzer system further configured to perform the steps of:
   determining a diagnosis of a disease or a medical condition for the sample gas based on comparing a range of concentration values of the specified component for the disease or the medical condition with the concentration of the specified component in the sample gas.

17. The system of claim 14, wherein:
   the disease or the medical condition is asthma;
   the specified component is NO; and
   a lower bound on the range of concentration values for the specified component is 20 ppb.

18. The system of claim 14, wherein:
   the disease or the medical condition is acute lung injury;
   the specified component is isoprene; and
   a lower bound on the range of concentration values for the specified component is 12 nmol/liter.

* * * * *